(12) United States Patent
Baranton et al.

(10) Patent No.: US 11,567,349 B2
(45) Date of Patent: Jan. 31, 2023

(54) OPTICAL DEVICE ADAPTED TO BE WORN BY A WEARER

(71) Applicant: Essilor International, Charenton-le-Pont (FR)

(72) Inventors: Konogan Baranton, Charenton-le-Pont (FR); Benjamin Rousseau, Charenton-le-Pont (FR); Bruno Fermigier, Charenton-le-Pont (FR); Isabelle Poulain, Charenton-le-Pont (FR); Delphine Tranvouez-Bernardin, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 643 days.

(21) Appl. No.: 16/495,561

(22) PCT Filed: Mar. 20, 2018

(86) PCT No.: PCT/EP2018/057043
§ 371 (c)(1),
(2) Date: Sep. 19, 2019

(87) PCT Pub. No.: WO2018/172366
PCT Pub. Date: Sep. 27, 2018

(65) Prior Publication Data
US 2020/0018991 A1    Jan. 16, 2020

(30) Foreign Application Priority Data
Mar. 21, 2017  (EP) ..................... 17305313

(51) Int. Cl.
*G02C 7/08*    (2006.01)
*G02C 11/00*   (2006.01)
(Continued)

(52) U.S. Cl.
CPC .............. *G02C 7/083* (2013.01); *A61B 3/113* (2013.01); *G02B 27/0093* (2013.01); *G02C 11/10* (2013.01); *G02C 2202/20* (2013.01)

(58) Field of Classification Search
CPC ........ G02C 7/081–085; G02C 2202/20; A61B 3/113; G02B 3/14; G02B 27/0093
See application file for complete search history.

(56) References Cited

U.S. PATENT DOCUMENTS 11,221,488 B1 * 1/2022 Kangas ................... G02F 1/294
2014/0218647 A1 * 8/2014 Blum ............... B29D 11/00009
349/13
(Continued)

FOREIGN PATENT DOCUMENTS

DE  10 2015 214 671 A1  2/2017
DE     102015214671 A1 * 2/2017 ............. A61B 3/103
(Continued)

OTHER PUBLICATIONS

English machine translation of DE-102015214671-A1 (Year: 2017).*
International Search Report and Written Opinion dated Jun. 19, 2018 in PCT/EP2018/057043 filed on Mar. 20, 2018.

Primary Examiner — Nicholas R. Pasko
(74) Attorney, Agent, or Firm — Oblon, McClelland, Maier & Neustadt, L.L.P.

(57) ABSTRACT

The invention relates to an optical device (10) adapted to be worn by a wearer comprising at least: —a programmable lens (20) having an adjustable optical function and extending between at least one eye of the wearer and the real world scene when the optical device is worn by the wearer, —an optical function controller (30) comprising —a memory (32) storing at least computer executable instructions; and —a processor (34) for executing the stored computer executable instructions so as to control the optical function of the programmable lens (20), wherein the computer executable
(Continued)

instructions comprise instructions for adjusting the optical function of the programmable lens (20) over a period of time determined so that the wearer does not perceive the adjustment of the optical function.

16 Claims, 1 Drawing Sheet

(51) Int. Cl.
*A61B 3/113* (2006.01)
*G02B 27/00* (2006.01)

(56) References Cited

U.S. PATENT DOCUMENTS

| | | | |
|---|---|---|---|
| 2014/0347623 A1* | 11/2014 | Inoue | G02B 27/0093 |
| | | | 351/159.41 |
| 2017/0059886 A1 | 3/2017 | Fayolle et al. | |
| 2021/0132414 A1* | 5/2021 | Peloux | G02B 27/0093 |

FOREIGN PATENT DOCUMENTS

| WO | WO 2014/179857 A1 | 11/2014 | | |
|---|---|---|---|---|
| WO | WO-2014179857 A1 * | 11/2014 | | A61B 3/113 |

\* cited by examiner

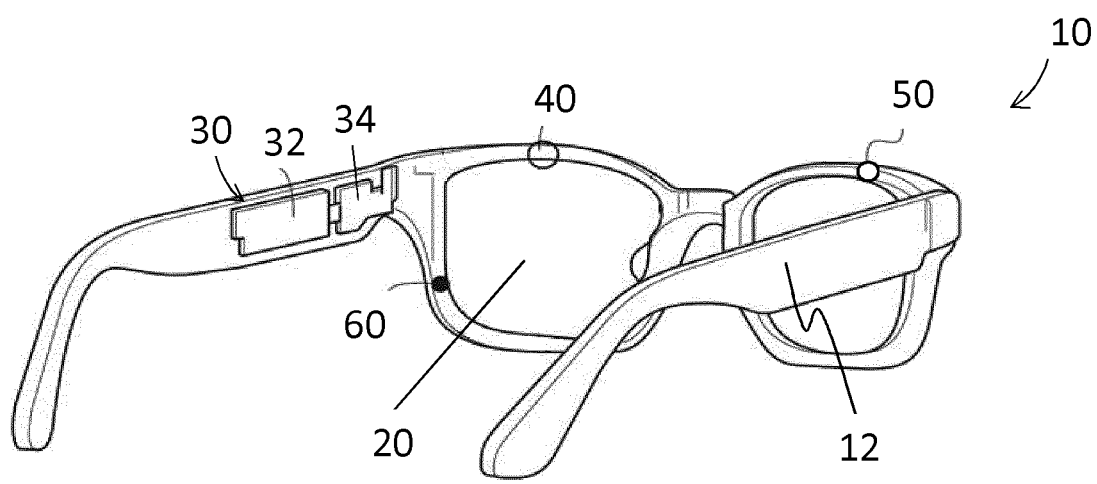

OPTICAL DEVICE ADAPTED TO BE WORN BY A WEARER

FIELD OF THE INVENTION

The invention relates to an optical device adapted to be worn by a wearer comprising a programmable lens and an optical function controller.

BACKGROUND OF THE INVENTION

Usually, an active lens permits a variation of the optical power or prism of the lens while being worn by a wearer. For instance, it exists active lenses with a manual adjustment of the optical power or prism of the lens.

When focused on the wearer's needs, an active lens induces a variable prismatic deviation and a strong and disturbing apparent motion appears.

It exists active lenses, such as Fresnel lenses with additional power limited to field of view of the wearer, which are automatically activated when the wearer lows his head. Plus, it exists active lenses comprising an optical component stacked between two perpendicular active Fresnel cylindrical lenses. In order to maintain a fine central vision, the resulting spherical power is centered according a fixation point. In both cases, the optical function seen by the wearer is equivalent to a mobile patch skating or jumping on the lens according to his gaze direction or to his head orientation which moreover may occur at the wrong time.

Moreover, it exists active lenses controlled by adjusting the optical power according to vergence measurement with an eye-tracker. However, such active lenses have a high latency and are not sufficiently accurate. Indeed, eye-trackers with vergence measurement are not able to guarantee any precision, even on a restricted field of view, and thus the unprecise vergence measurement cause an unstable vision. It also exists high end devices, for instance used in sciences to study vergence, but such devices are heavy.

Furthermore, it exists other techniques to control the optical power, based on the gaze direction and on a three-dimensional scan, to avoid vergence measurement, or on salience mapping of the environment, but such techniques are not compatible with wearable devices.

In all cases, embedded gaze-tracking devices have high power consumption, latency, errors and dysfunction. Such limitation are, for instance, noticeable while a wearer sits and uses his phone, or his tablet, or his computer, or when a wearer is at the top of a stair and lows his head to adjust his foot placement to go down. The steps of the stair can suddenly move, according to the head motion, the eye-tracker calibration, or the lighting, and the wearer can fall down. Indeed, it may cause a misaligned and blurred vision while descending the stairs.

Thus, there is a need for an optical device adapted to be worn by a wearer for adjusting the optical function of the optical device while the optical device is worn by the wearer to circumvent such limitations.

A control loop of the optical function based on gaze direction need to be very finely adjusted to avoid unbearable oscillations or drifts.

One object of the invention is to provide such an optical device.

SUMMARY OF THE INVENTION

To this end, the invention proposes an optical device adapted to be worn by a wearer comprising at least:

a programmable lens having an adjustable optical function and extending between at least one eye of the wearer and the real world scene when the optical device is worn by the wearer, an optical function controller comprising
  a memory storing at least computer executable instructions; and
  a processor for executing the stored computer executable instructions so as to control the optical function of the programmable lens, wherein the computer executable instructions comprise instructions for adjusting the optical function of the programmable lens over a period of time determined so that the wearer does not perceive the adjustment of the optical function.

Advantageously, the optical device according to the invention allows a variation of the optical function while the optical device is worn by the wearer.

The optical function of the programmable lens may be adjusted over a period of time during which the wearer does not perceive the adjustment of the optical function.

Advantageously, the optical device according to the invention allows a higher comfort for the wearer.

According to embodiments, the optical device according to the invention may further comprise one or several of the following features according to any possible combination:

the optical device comprises an eye sensor adapted to measure eye data relating to the eye movement of the wearer using the optical device and wherein the computer executable instructions comprise instructions for adjusting the optical function of the programmable lens when the eye data indicate that the at least one eye of the wearer is closed; and/or the computer executable instructions comprise instructions for adjusting the optical function of the programmable lens at a rate below the perception rate of the wearer; and/or the optical device comprises a vision sensor adapted to measure vision data relating to the vision direction and/or vision distance of said at least one eye of the wearer using the optical device and wherein the computer executable instructions comprise instructions for adjusting the optical function of the programmable lens when the vision data indicate an ocular saccade of the at least one eye of the wearer; and/or the computer executable instructions comprise instructions for adjusting the optical function of the programmable lens when the vision data indicate a vertical and/or horizontal ocular saccade of the at least one eye of the wearer; and/or the vision sensor is adapted to measure at least two consecutive ocular saccades, and wherein the computer executable instructions comprise instructions for adjusting the optical function of the programmable lens when the vision data indicate the second ocular saccade of the at least one eye of the wearer; and/or the computer executable instructions comprise instructions for adjusting the dioptric function of the programmable lens; and/or the computer executable instructions comprise instructions for adjusting the optical power of the programmable lens; and/or the optical device comprises a vision sensor adapted to measure vision data relating to the vision direction and/or vision distance of the wearer using the optical device and wherein the computer executable instructions comprise instructions for moving the optical power of the programmable lens with the vision direction of the wearer; and/or the optical device comprises a position sensor adapted to measure position data relating to the position of a reference point of the programmable lens of the optical device relative to a reference point of an eye of the wearer and wherein the computer executable instructions comprise instructions for adjusting the optical power of the programmable lens based on the position data; and/or the optical function of the programmable lens comprises a Fresnel optical function and the computer executable instructions comprise instructions for adjusting the position of the central ring of the Fresnel optical function to correspond to the vision direction of said at least one eye of the wearer using the optical device; and/or the computer executable instructions comprise instructions for adjusting the sphere power of the central ring of the Fresnel optical function based on the vision distance of said at least one eye of the wearer using the optical device; and/or the adjustment of the optical power of the programmable lens is smaller than or equal to 0.25D; and/or the adjustment of the optical power of the programmable lens is smaller than or equal to 0.12D; and/or the computer executable instructions comprise instructions for adjusting the prism of the programmable lens in at least one position of the programmable lens; and/or the computer executable instructions comprise instructions for adjusting the transmission function of the programmable lens; and/or the optical device comprises comprising at least two programmable lenses having adjustable optical functions and extending respectively between the right and left eyes of the wearer and the real world scene when the optical device is worn by the wearer, and wherein the computer executable instructions comprise instructions for adjusting the optical function of both programmable lenses over a period of time determined so that the wearer does not perceive the adjustment of the optical function; and/or the computer executable instructions comprise instructions for adjusting the optical functions of both programmable lenses independently one from the other; and/or the computer executable instructions comprise instructions for adjusting the optical function of the programmable lens (20) gradually at such a rate that the wearer does not perceive that the optical function is different between two consecutive values of optical function.

Unless specifically stated otherwise, as apparent from the following discussions, it is appreciated that throughout the specification discussions utilizing terms such as "computing", "calculating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. This apparatus may be specially constructed for the desired purposes, or it may comprise a general purpose computer or Digital Signal Processor ("DSP") selectively activated or reconfigured by a computer program stored in the computer. Such a computer program may be stored in a computer readable storage medium, such as, but is not limited to, any type of disk including an application specific integrated circuit (ASIC), floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus.

The processes presented herein are not inherently related to any particular computer or other apparatus. Various general purpose systems may be used with programs in accordance with the teachings herein, or it may prove convenient to construct a more specialized apparatus to perform the desired method. The desired structure for a variety of these systems will appear from the description below.

In addition, embodiments of the present invention are not described with reference to any particular programming language. It will be appreciated that a variety of programming languages may be used to implement the teachings of the inventions as described herein.

BRIEF DESCRIPTION OF THE DRAWINGS

Other characteristics and advantages of the invention will become more apparent from the claims and from the following description of some embodiments given by way of example without limitation with reference to the drawings, in which:

FIG. 1 is an optical device according to the invention.

Elements in the figures are illustrated for simplicity and clarity and have not necessarily been drawn to scale. For example, the dimensions of some of the elements in the FIGURE may be exaggerated relative to other elements to help improve the understanding of the embodiments of the present invention.

DETAILED DESCRIPTION OF PREFERRED EMBODIMENTS

The invention relates to an optical device adapted to be worn by a wearer. The optical device 10 may be a head mounted device, as represented in FIG. 1, comprising a frame 12.

The optical device 10 comprises at least one, for instance two, programmable lens 20. The programmable lens 20 may be an active programmable lens. The programmable lens 20 has an adjustable optical function. The programmable lens 20 is configured to extend between at least one eye of the wearer and the real world scene when the optical device is worn by the wearer.

The optical device 10 comprises an optical function controller 30. The optical function controller 30 comprises a memory 32 and a processor 34.

The memory 32 is configured to store computer executable instructions. The memory 32 may also be configured to store data received by the optical function controller 30.

The processor 34 is configured to execute the stored computer executable instructions so as to control the optical function of the programmable lens 20.

The computer executable instructions comprise instructions for adjusting the optical function of the programmable lens 20 over a period of time determined so that the wearer does not perceive the adjustment of the optical function.

In particular, the computer executable instructions may comprise instructions for adjusting the optical function of the programmable lens 20 over a period of time determined so that the adjustment of the optical function corresponds to wearer's preferences or to wearer's needs, and more precisely to the wearer's visual preferences or to the visual wearer's needs.

For instance, the predetermined period of time is smaller than 50 ms. Preferably, the predetermined period of time is smaller than 20 ms so that the wearer does not perceive the adjustment of the optical function.

The adjustment of the optical function may be applied on a part of the field of view of the wearer or in the whole field of view of the wearer. In other words, the adjustment of the optical function may be applied on a part of the programmable lens, or on the whole programmable lens. For instance, the optical function may remain constant in the central vision of the wearer and may be adjusted in the peripheral vision of the wearer.

The optical function may comprise the dioptric function, the light absorption, the polarizing capability or the reinforcement of contrast capacity.

The dioptric function corresponds to the programmable lens power, for instance the mean power or the astigmatism, as a function of the gaze direction.

The optical function of the optical device may comprise a sun protection function, for example by controlling a transmission parameter of the programmable lens or the polarization of a surface of the programmable lens.

The programmable lens 20 may be an optical lens, an ophthalmic lens, a spectacle lens, a progressive or single vision lens.

The programmable lens 20 may comprise a succession of single vision, for instance unifocal, designs on the lens, or a succession of progressive power lenses. By using a succession of progressive power lenses, instead of a succession of single vision designs, the number of transition states for the adjustment of the programmable lens is reduced, and thus, the risk of potential discomfort of the wearer is limited.

For instance, a wearer suffering from presbyopia, may practice three different activities at different gazing distance. The wearer may need a far vision correction, for example for watching TV or driving, an intermediate vision correction, for example for looking at his computer, and a near vision correction, for example for looking at his phone or reading a book. If a succession of single vision corrections on the programmable lens is used, when the wearer needs to use the far vision correction, then the intermediate vision correction, and then the near vision correction, three different corrections adapted to the three different distances need to be proposed. Hence, two transitions states for the adjustment are managed. However, if a succession of progressive power lenses corrections on the programmable lens is used, the wearer may have a first vision correction adapted to the far and intermediate vision activities and a second vision correction for the intermediate and near vision activities. If the wearer needs to use the far vision correction, then the intermediate vision correction, and then the near vision correction, only one transition is managed, and thus the number of transition states is reduced relative to the use of a succession of single vision corrections on the programmable lens.

Additionally, the progressive lens may comprise a progressive power lens or a succession of progressive power lenses.

Advantageously, using a succession of progressive power lenses, instead of a progressive power lens, reduces the optical constraints. For instance, by adapting the progressive power lens to activities that need a specific vision distance, the amount of power added by the programmable lens is reduced. Indeed, for a distance vision from 33 cm to the infinite, a greater value of power is needed on a progressive power lens than on a succession of progressive power lenses, for instance comprising two progressive power lenses, one being adapted for a distance vision from 33 cm to 63 cm, the other being adapted for a distance vision from 63 cm to the infinite.

Moreover, the fields of view of a succession of progressive power lenses are larger, more stable and adapted to the activity of the wearer over the time, than the field of view of a progressive power lens where the intermediate vision can be less stable and narrower than the far vision. Plus, for a succession of progressive power lenses, the quantity of aberrations in the periphery is reduced relative to in a progressive power lens. The progression length of a succession of progressive power lenses may be adapted to the activities and reduced to be closer to a "natural" near vision posture than on a progressive power lens where the near vision may be located too low in the lens due to conception or fabrication constraints.

The use of a succession of progressive power lenses may free the direction or axis of the variation of the power on the programmable lens. Hence, the direction of the variation of the power may vary in the programmable lens, depending on the activity of the wearer. For example, instead of having a variation from the upper part to the lower part of the lens, the situation may be switched to have a near vision correction in the upper part of the lens, for postures that are different than classical ones, for example for fixing something on a wall, or watching TV lying on a sofa, or reading a book lying in a bed. Plus, a variation in a different direction, like into the left or into the right, for other specific activities may also be managed.

The optical device 10 may comprise an eye sensor 40. In the sense of the invention, an eye sensor 40 is an eyeball sensor, for instance an eyeball rotation sensor or an eyeball position sensor, or an eyelid sensor. The eye sensor 40 is adapted to measure eye data relating to the eye movement of the wearer using the optical device 10.

The computer executable instructions may comprise instructions for adjusting the optical function of the programmable lens 20 when the eye data indicate that the eye of the wearer is closed. In other words, the computer executable instructions may comprise instructions for adjusting the optical function of the programmable lens 20 when an eye-blink of the wearer is detected.

An eye-blink is a fast closing of an eyelid useful to, at least, spreads tears and cleans the surface of the cornea and conjunctiva. An eye-blink is also useful to protect the eye from damages, and cuts the wearer's attention, during tiredness or sleep.

The computer executable instructions may comprise instructions for adjusting the optical function of the programmable lens 20 at a rate below the perception rate of the wearer.

The adjustment of the optical function of the programmable lens may be done slowly, namely with a small step, such that the wearer does not perceive that the optical function is different between two consecutive values of optical function separated with the step. In other words, a prismatic deviation in at least one position of the programmable lens may be slowly introduced such that the adjustment of the optical function can be invisible for the wearer. More precisely, with a prismatic displacement gradually introduced on the programmable lens, the wearer may not be aware of the prismatic displacement on the programmable lens.

When the optical function is adjusted slowly, the perception rate of the wearer depends on the mobility of the wearer, namely depends on if the wearer is moving or not. In particular, when the wearer is moving, the optical function need to be adjusted slower than when the wearer is motionless in order to avoid an imbalance of the wearer.

When the wearer is motionless, if the wearer looks an image on his hand on a screen, as if he was looking through a window, and a lateral bias between the image and the real hand slowly introduced at 25 mm per second, namely at a variation of prism of 6 Diopter per second, such prismatic variation is not consciously perceived by the wearer, even with a shift above 10 cm.

When the wearer is moving, it is important to have a speed of variation in prism or deflection introduced by the programmable lens that does not disturb the motion activities of the wearer. The prismatic variation speed may be smaller than 1.75 prism diopters per second, and more precisely smaller than 0.85 prism diopters per second, when the wearer is in motion. Such prismatic variation speed corresponds to a situation where a wearer fixates a point on a side at 10 meters while walking.

The adjustment of the optical function of the programmable lens may be done quickly, namely with a high speed, such that the wearer does not perceive the moment when the optical function is adjusted. For instance, the adjustment of the optical function of the programmable lens may be done during an ocular saccade or an eye-blink.

The perception rate of the wearer is around 50 ms, and the optical function may be adjusted with a speed of adjustment smaller than 50° ms such that the wearer does not perceive the adjustment of the optical function.

The optical device 10 may comprise a vision sensor 50. The vision sensor 50 is adapted to measure vision data relating to the vision direction and/or vision distance of the eye of the wearer using the optical device 10. The vision sensor 50 may be a camera or an eye-tracking device. The speed of the ocular saccade, namely the rotation speed of the eyeball, may be taking onto account to indicate the size of the ocular saccade or the distance of the next fixation area.

The computer executable instructions may comprise instructions for adjusting the optical function of the programmable lens 20 when the vision data indicate an ocular saccade of the eye of the wearer.

An ocular saccade is a type of ocular motion, defined by a fast eye rotation from 100 degrees per second to more than 600 degrees per second.

Usually, an ocular saccade permits to move quickly the fovea, the high resolution area of the retina, towards a special point of interest to observe during fixations or pursuits, where the gaze direction is maintained aligned on an environment or a moving objet. During this very fast motion, in normal condition, without strobe or flash, an image cannot be perceived by the wearer due to its fast sliding on the retina.

In general, eye-blinks and ocular saccades are concomitant.

After an eye-blink or an ocular saccade, the eye position is naturally disrupted by error in carrying out the ocular saccade or a motion induced by the eyelid friction. A not perceived post reflex re-adjusts the gaze direction. The optical function, and for instance the prism, may be adjusted during an eye-blink or an ocular saccade so that the adjustment is not perceived by the wearer.

For instance, the wearer is looking through a first area of the programmable lens, and while exploring the environment, the wearer have an ocular saccade during which his gaze direction is moved toward a second area of the lens, for example distant from the first area. An eye-tracker is not able to measure this phenomenon, since it is comprised between 20 ms and 200 ms, which is too fast to be measured. When the wearer's gaze direction stays long enough in the second area, for instance 0.5 second or more, the gaze direction of the wearer may be measured and the programmable lens may adjust the prism in at least one position of the programmable lens during the next eye-blink or the ocular saccade. As an eye-blink may occur every 2 to 10 seconds and more than 2 ocular saccades may occur per second, the wearer's gaze direction may stay long enough in the second area, and it might be anticipated by the computer executable instructions if the programmable lens needs it. Such adjustment may be near from the previous value of the prism, for instance a difference between the two consecutive values of prism smaller than 5 degrees, which is the amplitude of a normal corrective ocular saccade. Such adjustment may be repeated and modulated according to specific criteria, such as the wearer's activity, for instance reading, watching a screen, doing manual activities, or moving.

The wearer's activity may be measured in real time by using an inertial measurement unit (IMU). An IMU comprises an accelerometer for detecting the frequency and the amplitude of the movement of the head of the wearer and a gyroscope.

The optical function of the programmable lens may be adjusted depending on the activity of the wearer detected by the IMU or indicated by the wearer, for instance in a list of pre-programmed activities. For instance, if a wearer do archery, even if the wearer moves, for example for catching an arrow, the optical function of the programmable lens may be maintained with the far vision correction. If a wearer paint a landscape, even if the wearer moves his head, the optical function of the programmable lens may be maintained with the far and intermediate or near vision correction. When adjusting the optical function during an eye-blink or ocular saccade, in order to remain not perceived by the wearer, the adjustment may be applied to the programmable lens before the end, or close to the end of the ocular saccade or eye-blink.

For instance, when using an optical device having a low speed programmable lens, the optical function may be adjusted at the beginning of the detection of an ocular saccade or eye-blink, in order to ensure that the adjustment of the optical function is finished before the end of the ocular saccade or eye-blink.

When using a high speed eye-tracker, for instance having a frequency between 50 Hertz and 500 Hertz, to acquire the position of the eye of the wearer in real time, the optical function may be adjusted with a high speed programmable lens during an ocular saccade or eye-blink, or at a time close to the end of the ocular saccade or eye-blink, for instance at a time smaller than 20 ms. When the adjustment of the optical function appears during an ocular saccade or eye-blink, the adjustment is not perceived by the wearer. The adjustment of the optical function may be accurate or may be an estimate, and after the ocular saccade or eye-blink, a high accuracy eye-tracking device can be conducted, for instance using the average of measurements of high speed and low accuracy eye-tracker, and a low adjustment of the optical function may be used to reach the desired optical function.

In particular, the optical function may be adjusted only during an ocular saccade or blink, and may not be adjusted, or may be slowly adjusted at other moments.

The computer executable instructions may comprise instructions for adjusting the optical function of the programmable lens 20 when the vision data indicate a vertical and/or horizontal ocular saccade of the eye of the wearer.

The vision sensor 50 may be adapted to measure consecutive ocular saccades, for instance two consecutive ocular saccades. The vision sensor 50 may be adapted to measure the speed of the ocular saccade so as to anticipate the next gaze position. The ocular saccade speed and the ocular saccade size may be determined from the behavior of the wearer.

The computer executable instructions may comprise instructions for adjusting the optical function of the programmable lens 20 when the vision data indicate a second ocular saccade of the eye of the wearer.

The eye sensor 40 may be adapted to measure consecutive blinks, for instance two consecutive blinks. The eye sensor 50 may be adapted to measure the time interval between consecutive blinks so as to anticipate the next blink. The interval between consecutive blinks may be determined from the behavior of the wearer. The computer executable instructions may comprise instructions for adjusting the optical function of the programmable lens 20 when the vision data indicate a second blink of the eye of the wearer. Moreover, it is known that reproducible successions of eye blinks, such as two eye blinks in a short succession, may occur due to a reflex favouring a uniform lachrymal film. Advantageously, the optical function may be adjusted during an anticipated eye blink.

The computer executable instructions may comprise instructions for adjusting the dioptric function or the optical power of the programmable lens 20. For instance, the optical power of the programmable lens may be adjusted by moving the optical power of the programmable lens with the vision distance of the wearer.

The optical device 10 may comprise a position sensor 60. The position sensor 60 is adapted to measure position data relating to the position of a reference point of the programmable lens 20 of the optical device 10 relative to a reference point of an eye of the wearer. The reference point of the eye of the wearer may be the center of rotation of the eye of the wearer. The position sensor 60 may be a capacitive sensor.

The computer executable instructions may comprise instructions for adjusting the optical power of the programmable lens 20 based on the position data. In other words, the position of the optical device relative to the wearers' head may be measured to adjust the optical power. More precisely, the frame of the optical device may slide on the nose of the wearer from a first, initial, position to a second, new, position, and the new position of the optical device may be taken into account for adjusting the optical function of the programmable lens.

Details on a head mounted device for monitoring the relative position of the head mounted device and the wearer of such head mounted device are disclosed in the application published under number WO 2016/156600 A2.

The adjustment of the optical power of the programmable lens 20 may be smaller than or equal to 0.25D, and preferably smaller than or equal to 0.12D.

The computer executable instructions may comprise instructions for adjusting the prism at least in one position of the programmable lens 20. The prism in at least one position of the programmable lens may be changed when modifying the spherical or cylindrical power or axis of the programmable lens at least in one position, and/or when modifying the optical center of the programmable lens, namely the position for which the prism is equal to zero.

The computer executable instructions may comprise instructions for adjusting the transmission function of the programmable lens 20.

The optical function of the programmable lens 20 may comprise a Fresnel optical function and the computer executable instructions may comprise instructions for adjusting the Fresnel optical function based on vision data from the vision sensor 50.

The position of the central ring of the Fresnel optical function may be adjusted to correspond to the vision direction of said at least one eye of the wearer using the optical device.

The sphere power of the central ring of the Fresnel optical function may be adjusted based on the vision distance of said at least one eye of the wearer using the optical device.

The abovementioned instructions for adjusting the dioptric function and/or the optical power and/or the prism and/or the transmission function and/or the Fresnel optical function of the programmable lens may correspond to adjustments over a period of time determined so that the wearer does not perceive the adjustment of the optical function.

The optical device 10 may comprise two programmable lenses 20, each programmable lens having an adjustable optical function. A programmable lens 20 extends between the right eye of the wearer and the real world scene when the optical device is worn by the wearer. The other programmable lens 20 extends between the left eye of the wearer and the real world scene when the optical device is worn by the wearer.

The computer executable instructions may comprise instructions for adjusting the optical function of both programmable lenses 20.

The computer executable instructions may comprise instructions for adjusting the optical functions of both programmable lenses 20 independently one from the other. For instance, if the wearer have different corrections for the right and left eyes, it may be advantageous to adjust the optical function of only one of the programmable lens, or to adjust the optical function of the programmable lenses independently one from the other. Moreover, only one of the optical functions of the programmable lenses may need to be adjusted. Plus, the right and left eyes of the wearer may have different sensitivities, and thus a different adjustment of the optical function may be needed for the right and left eyes. The programmable lenses may be adjusted at the same time or at different moments, according to the wearer's preferences or to the wearer's needs.

The invention has been described above with the aid of embodiments without limitation of the general inventive concept. Moreover, the embodiments of the invention may be combined without any restriction.

Many further modifications and variations will suggest themselves to those skilled in the art upon making reference to the foregoing illustrative embodiments, which are given by way of example only and which are not intended to limit the scope of the invention, that being determined solely by the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

The invention claimed is:

1. An optical device adapted to be worn by a wearer comprising:
   a programmable lens having an adjustable optical function and extending between at least one eye of the wearer and the real world scene when the optical device is worn by the wearer;
   an optical function controller including:
      a memory storing at least computer executable instructions; and
      a processor configured to execute the stored computer executable instructions to control the optical function of the programmable lens; and
   a vision sensor adapted to
      measure vision data relating to the vision direction and/or vision distance of said at least one eye of the wearer using the optical device,
      measure at least two consecutive ocular saccades, and measure ocular saccade speed,
   wherein the computer executable instructions further include instructions for anticipating a next gaze position based on the measured ocular saccade speed, and adjusting the optical function of the programmable lens when the vision data indicate the second ocular saccade of the two consecutive ocular saccades of the at least one eye of the wearer, and
   wherein adjusting the optical function of the programmable lens includes moving an area exhibiting an optical power of the programmable lens with the vision direction of the wearer.

2. The optical device according to claim 1, further comprising an eye sensor adapted to measure eye data relating to the eye movement of the wearer using the optical device and wherein the computer executable instructions comprise instructions for adjusting the optical function of the programmable lens when the eye data indicate that the at least one eye of the wearer is closed.

3. The optical device according to claim 1, wherein the computer executable instructions comprise instructions for adjusting the optical function of the programmable lens over a predetermined period of time smaller than 50 ms.

4. The optical device according to claim 1, wherein the computer executable instructions comprise instructions for adjusting the optical function of the programmable lens when the vision data indicate a vertical and/or horizontal ocular saccade of the at least one eye of the wearer.

5. The optical device according to claim 1, wherein the computer executable instructions comprise instructions for adjusting the dioptric function of the programmable lens.

6. The optical device according to claim 1, wherein the computer executable instructions comprise instructions for adjusting a prism of the programmable lens in at least one position of the programmable lens.

7. The optical device according to claim 1, wherein the computer executable instructions comprise instructions for adjusting a transmission function of the programmable lens.

8. The optical device according to claim 1, comprising at least two programmable lenses having adjustable optical functions and extending respectively between the right and left eyes of the wearer and the real world scene when the optical device is worn by the wearer, and wherein the computer executable instructions comprise instructions for adjusting the optical function of both programmable lenses over a period of time determined to reduce perception of the adjustment of the optical function, and
   wherein the predetermined period of time is smaller than 50 ms.

9. The optical device according to claim 1, wherein the computer executable instructions comprise instructions for adjusting the optical function of the programmable lens gradually at such a rate to reduce perception of the optical function being different between two consecutive values of optical function, and
   wherein the perception rate of the wearer is 50 ms.

10. The optical device according to claim 1, wherein the optical function of the programmable lens comprises a Fresnel optical function and the computer executable instructions comprise instructions for adjusting the position of the central ring of the Fresnel optical function to correspond to the vision direction of said at least one eye of the wearer using the optical device.

11. The optical device according to claim 10, wherein the computer executable instructions comprise instructions for adjusting the sphere power of the central ring of the Fresnel optical function based on the vision distance of said at least one eye of the wearer using the optical device.

12. The optical device according to claim 1, wherein the computer executable instructions comprise instructions for adjusting the optical power of the programmable lens.

13. The optical device according to claim 12, further comprising the vision sensor adapted to measure vision data relating to the vision direction of the wearer using the optical device and wherein the computer executable instructions comprise instructions for moving the optical power of the programmable lens with the vision direction of the wearer.

14. The optical device according to claim 12, further comprising a position sensor adapted to measure position data relating to the position of a reference point of the programmable lens of the optical device relative to a reference point of an eye of the wearer and wherein the computer executable instructions comprise instructions for adjusting the optical power of the programmable lens based on the position data.

15. The optical device according to claim 12, wherein the adjustment of the optical power of the programmable lens is smaller than or equal to 0.25D.

16. The optical device according to claim 12, wherein the adjustment of the optical power of the programmable lens is smaller than or equal to 0.12D.

* * * * *